United States Patent
Ley et al.

(10) Patent No.: US 7,060,089 B2
(45) Date of Patent: Jun. 13, 2006

(54) MULTI-LAYER STENT

(75) Inventors: Timothy J. Ley, Shoreview, MN (US); Brian J. Brown, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 548 days.

(21) Appl. No.: 10/055,307

(22) Filed: Jan. 23, 2002

(65) Prior Publication Data
US 2003/0139799 A1    Jul. 24, 2003

(51) Int. Cl.
*A61F 2/06* (2006.01)
(52) U.S. Cl. .................. 623/1.15; 606/196
(58) Field of Classification Search ............... 606/198; 623/1.15, 1.1, 1.11, 1.12, 1.13, 1.14, 1.16–1.18, 623/1.2
See application file for complete search history.

(56) References Cited

U.S. PATENT DOCUMENTS

| | | | |
|---|---|---|---|
| 4,503,569 A | 3/1985 | Dotter | 3/1.4 |
| 4,512,338 A | 4/1985 | Balko et al. | 128/1 R |
| 4,732,152 A | 3/1988 | Wallsten et al. | 128/343 |
| 4,733,665 A | 3/1988 | Palmaz | 606/108 |
| 4,768,507 A | 9/1988 | Fischell et al. | 128/303 R |
| 4,820,298 A | 4/1989 | Leveen et al. | 623/1 |
| 4,830,003 A | 5/1989 | Wolff et al. | 128/343 |
| 4,848,343 A | 7/1989 | Wallsten et al. | 128/343 |
| 4,886,062 A | 12/1989 | Wiktor | 128/343 |
| 4,907,336 A | 3/1990 | Gianturco | 29/515 |
| 4,990,155 A | 2/1991 | Wilkoff | 606/191 |
| 5,019,090 A | 5/1991 | Pinchuk | 606/194 |
| 5,234,456 A | 8/1993 | Silvestrini | 606/194 |
| 5,258,020 A | 11/1993 | Froix | 623/1 |
| 5,258,027 A * | 11/1993 | Berghaus | 623/9 |
| 5,443,458 A | 8/1995 | Eury | 604/891.1 |
| 5,618,299 A | 4/1997 | Khosravi et al. | 606/198 |
| 5,645,559 A | 7/1997 | Hachtman et al. | 606/198 |
| 5,667,523 A * | 9/1997 | Bynon et al. | 623/1.13 |
| 5,755,770 A | 5/1998 | Ravenscroft | 623/1 |
| 5,755,781 A | 5/1998 | Jayaraman | 623/1 |
| 5,769,887 A | 6/1998 | Brown et al. | 623/1 |
| 5,824,046 A | 10/1998 | Smith et al. | 623/1 |
| 5,843,120 A | 12/1998 | Israel et al. | 606/198 |
| 5,843,168 A | 12/1998 | Dang | 623/1 |
| 5,855,597 A | 1/1999 | Jayaraman | 623/1 |
| 5,873,906 A | 2/1999 | Lau et al. | 623/1 |

(Continued)

FOREIGN PATENT DOCUMENTS

CA    2025626    9/1990

(Continued)

*Primary Examiner*—Julian W. Woo
*Assistant Examiner*—Victor Nguyen
(74) *Attorney, Agent, or Firm*—Vidas, Arrett, Steinkraus (57) ABSTRACT

A stent may be formed having a reduced state and an expanded state. The stent having a longitudinal axis therethrough. The stent comprises at least one serpentine segment having a proximal end and a distal end. The serpentine segment comprises a plurality of peaks and troughs, wherein the peaks are disposed at the distal end of the segment and the troughs are disposed at the proximal end of the segment. The peaks include first peaks and second peaks arranged in a regular alternating pattern about the longitudinal axis. In the reduced state the first peaks disposed at a first distance from the longitudinal axis of the stent and the second peaks disposed at a second distance from the longitudinal axis of the stent. The second distance is less than the first distance. The first peaks defining a substantially cylindrical outer surface of the segment.

6 Claims, 12 Drawing Sheets

U.S. PATENT DOCUMENTS

| | | | |
|---|---|---|---|
| 5,916,234 A | 6/1999 | Lam | 606/198 |
| 5,957,930 A | 9/1999 | Vrba | 606/108 |
| 5,980,565 A | 11/1999 | Jayaraman | 623/1 |
| 6,056,767 A | 5/2000 | Boussignac et al. | 606/194 |
| 6,083,257 A | 7/2000 | Taylor et al. | 623/1 |
| 6,099,559 A | 8/2000 | Nolting | 623/1.16 |
| 6,120,522 A | 9/2000 | Vrba et al. | 606/190 |
| 6,123,712 A | 9/2000 | Di Caprio et al. | 606/108 |
| 6,152,957 A | 11/2000 | Jang | 623/1.37 |
| 6,176,872 B1 | 1/2001 | Miksza | 623/1.15 |
| 6,214,037 B1 | 4/2001 | Mitchell et al. | 623/1.11 |
| 6,231,598 B1 * | 5/2001 | Berry et al. | 623/1.15 |
| 6,287,335 B1 | 9/2001 | Drasler et al. | 623/1.28 |
| 6,334,869 B1 * | 1/2002 | Leonhardt et al. | 623/1.13 |
| 6,340,366 B1 | 1/2002 | Wijay | 623/1.13 |
| 6,348,065 B1 * | 2/2002 | Brown et al. | 623/1.16 |
| 6,383,171 B1 | 5/2002 | Gifford et al. | 604/508 |
| 6,383,216 B1 | 5/2002 | Kavteladze et al. | 623/1.22 |
| 6,547,818 B1 | 4/2003 | Rourke et al. | 623/1.16 |
| 6,565,597 B1 | 5/2003 | Fearnot et al. | 623/1.14 |
| 6,579,310 B1 | 6/2003 | Cox et al. | 623/1.16 |
| 6,673,106 B1 | 1/2004 | Mitelberg et al. | 623/1.12 |
| 6,776,793 B1 * | 8/2004 | Brown et al. | 623/1.15 |
| 2003/0139799 A1 | 7/2003 | Ley et al. | 623/1.15 |

FOREIGN PATENT DOCUMENTS

| | | |
|---|---|---|
| CA | 2008312 | 5/2000 |
| DE | 197 46 882 A1 | 4/1999 |
| EP | 0 878 173 B1 | 8/2000 |
| WO | 96/14808 | 5/1996 |
| WO | 96/26689 | 9/1996 |
| WO | 98/14137 | 4/1998 |
| WO | 99/30638 | 6/1999 |
| WO | 00/71052 A1 | 11/2000 |
| WO | 01/06952 A1 | 2/2001 |
| WO | 01/85064 A1 | 11/2001 |
| WO | 02/13725 | 2/2002 |

* cited by examiner

MULTI-LAYER STENT

BACKGROUND OF THE INVENTION

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Stents are generally tubular in configuration, open ended and are expandable between a generally unexpanded insertion diameter and an expanded implantation diameter. Stents are commonly placed or implanted by a mechanical transluminal procedure.

Inflation expandable stents are well known and widely available in a variety of designs and configurations. Inflation expandable stents are crimped to their reduced diameter about the delivery catheter, then maneuvered to the deployment site and expanded to the vessel diameter by fluid inflation of a balloon positioned between the stent and the delivery catheter. The present invention is directed to all forms of stents including balloon expandable stents, self expanding stents and/or hybrid stents.

An example of a balloon expandable stent is shown in U.S. Pat. No. 5,843,120. An example of a self-expanding stent is described in WO 96/26689.

U.S. Pat. Nos. 4,733,665; 5,019,090; 4,503,569; 4,512,338; describe various stent configurations. U.S. Pat. Nos. 4,732,152 and 4,848,343 describe self-expanding stents.

Stents have been made using materials of varied composition and conformation. U.S. Pat. No. 4,768,507 describes a stent constructed of stainless steel, and a titanium alloy. U.S. Pat. No. 4,820,298 describes a stent having a flexible tubular body made from a thermal plastic to the form of a helix. Polyester and polycarbonate copolymers are selected as particularly desirable materials. U.S. Pat. No. 4,830,003 describes a stent made from wires formed into a cylinder. The wires are made of a biocompatible metal. Biocompatible metals include 300 series stainless steels such as 316 LS, as well as platinum and platinum iridium alloys, cobalt chromium alloys such as MP35N, and unalloyed titanium. U.S. Pat. No. 4,886,062 describes a stent made from low memory metal such as a copper alloy, titanium, tantalum, nitinol or gold. U.S. Pat. No. 4,907,336 describes a wire stent having malleable materials such as annealed stainless steels, tungsten and platinum in its construction.

Canadian Application 2,025,626, describes a bio degradable infusion stent of extruded material. The stent may incorporate radiopaque materials such as barium sulfate. U.S. Pat. No. 4,990,155 describes a plastic stent having an inherently expandable coil conformation. Materials of construction include high density polyethylene. Optionally, this material is compounded with an anti coagulant and/or an x ray opaque material such as bismuth sub carbonate. Canadian Patent Application 2,008,312, describes a stent made from a malleable flat sheet having a reticulated pattern.

There are also stents which deliver agents or drugs to blood passing through the vein or artery that are generally beneficial to the recipient. In addition, stents can deliver drugs or biologically active agents at a controlled rate to blood passing through the vessel lumen as well as to the vessel wall. U.S. Pat. No. 5,234,456 describes a hydrophilic stent comprising a wall structure where at least a portion thereof is a hollow wall in which a hydrophilic material for drug delivery is placed. U.S. Pat. 5,443,458 is directed to a multilayer laminated resorbable stent having a structural layer and additional layers stated to release drugs at predictable rates. U.S. Pat. No. 5,258,020 describes a self-restrained stent with an elastic memory, the stent optionally being formulated to provide for drug administration.

Stents are placed or implanted within a blood vessel for treating stenoses, strictures or aneurysms therein. They are implanted to reinforce collapsing, partially occluded, weakened, or dilated sections of a blood vessel. They have also been implanted in other bodily vessels including arteries, veins, biliary ducts, urethras, fallopian tubes, bronchial tubes, the trachea and the esophagus.

Typically, a stent will have a smaller, unexpanded cross-section or diameter for placement in a vessel and a larger, expanded cross-section or diameter after placement in the vessel or the duct. The ratio of the diameter of the expanded stent to the diameter of the unexpanded stent is referred to as the expansion ratio of the stent. Most current stent designs are limited in their ability to achieve large expansion ratios. Specifically, it is difficult to reduce the profile of a stent substantially beyond the diameter of the tubing from which the stents were cut or, in the case of a stent formed from a sheet, beyond the initial diameter of the tube formed from the sheet.

There remains a need for stents which have a reduced diameter or profile and yet are flexible in the unexpanded state to facilitate delivery of the stent and which are characterized by a large expansion ratio.

All U.S. patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

The abstract provided herewith is intended to comply with 37 CFR 1.72 and is not intended be used in determining the scope of the claimed invention.

BRIEF SUMMARY OF THE INVENTION

In one embodiment, the invention is directed to a stent comprising at least one serpentine segment. The serpentine segment comprises a plurality of peaks at the distal end of the segment and troughs at the proximal end of the segment. The peaks include first peaks and second peaks arranged in a regular alternating pattern about the longitudinal axis of the stent. The first peaks are disposed at a first distance from the longitudinal axis of the stent and the second peaks are disposed at a second distance from the longitudinal axis of the stent. The second distance is less than the first distance. The first peaks define a substantially cylindrical outer surface of the segment. Optionally, the second peaks may be arranged to define a substantially cylindrical inner surface of the segment. The substantially cylindrical inner surface of the segment may be arranged to taper outward toward the substantially cylindrical outer surface of the segment.

The stent may be in an expanded configuration or, desirably, in an unexpanded configuration. Also desirably, when the stent is expanded to an expanded configuration, the first and second peaks are equidistant from the longitudinal axis of the stent.

The troughs of the inventive stent may include first troughs and second troughs with the first troughs disposed at a first distance from the longitudinal axis of the stent and the second troughs disposed at a second distance from the longitudinal axis of the stent where the second distance is different from the first distance.

Optionally, the stent comprises a plurality of serpentine segments. Serpentine segments which are adjacent one another may be connected one to the other.

In another embodiment, the invention is directed to a tubular stent comprising at least one segment. The distal end of the segment comprises a plurality of distal closed portions and distal open portions alternating with one another. The distal closed portions include first distal closed portions disposed at a first distance from the longitudinal axis of the stent and second distal closed portions disposed at a second distance from the longitudinal axis of the stent where the second distance is less than the first distance. The first and second distal closed portions alternate with one another about the longitudinal axis of the stent. The first distal closed portions define a substantially cylindrical outer surface of the segment. The proximal end of the segment comprises a plurality of proximal closed portions and proximal open portions alternating with one another. The stent may be in an expanded state or, desirably, in an unexpanded state. In the latter case, when the stent expands into an expanded configuration, desirably the first and second distal closed portions are equidistant from the longitudinal axis of the stent.

Optionally, the proximal closed portions may include first proximal closed portions disposed at a first distance from the longitudinal axis of the stent and second proximal closed portions disposed at a second distance from the longitudinal axis of the stent, where the second distance is different from the first distance. The first and second proximal closed portions may be arranged in a regular pattern relative to the longitudinal axis of the stent. The second closed portions may define a substantially cylindrical inner surface of the segment. Optionally, the substantially cylindrical inner surface of the segment may taper outward towards the substantially cylindrical outer surface of the segment.

Any suitable segment may be used including serpentine segments and segments having a plurality of cells with openings therethrough. The proximal closed portions may be aligned or unaligned with the distal closed portions.

In yet another embodiment, the invention is directed to a stent comprising at least one segment. The distal end of the segment comprises a plurality of distal closed portions and distal open portions alternating with one another. Distal closed portions which are adjacent one another are arranged in overlapping relationship about the segment. The proximal end comprises a plurality of proximal closed portions and proximal open portions alternating with one another. The stent may be in an expanded state or, desirably, in an unexpanded state. In the latter case, when the stent expands into an expanded configuration, desirably the first and second distal closed portions are equidistant from the longitudinal axis of the stent.

The stent may comprise a plurality of struts extending between the distal closed portions and the proximal closed portions. The struts including a plurality of first struts and a plurality of second struts with the first struts extending from the proximal end of the segment to the distal end of the segment and defining a tubular outer surface of the stent. The second struts extend from the proximal end of the segment to the distal end of the segment and at least partially inward from the tubular outer surface of the stent toward the longitudinal axis of the stent.

Any suitable segment may be used including serpentine segments and segments which include a plurality of cells with openings therethrough. Where a plurality of segments are provided, segments which are adjacent one another may be connected to one another.

In another embodiment, the invention is directed to a stent in an unexpanded state comprising at least a first segment and a second segment with at least one connector extending therebetween. The first and second segments define a tubular outer surface of the stent. At least a portion of the connector includes a radial component, the portion not lying on the tubular surface of the stent. Optionally, the stent comprises a plurality of connectors extending between the first and second segments where at least a portion of each connector includes a radial component which does not lie on the tubular surface of the stent.

In yet another embodiment, the invention is directed to a stent comprising a plurality of cylindrical segments each of which is formed of a plurality of interconnected struts. The cylindrical segments include a first cylindrical segment and a second cylindrical segment connected to the first segment where at least a portion of the first segment and at least a portion of the second segment are in overlapping relationship when the stent is in an unexpanded state and in a non-overlapping relationship when the stent is in an expanded state. Desirably, the stent comprises at least three cylindrical segments, adjacent segments of which are in overlapping relationship with one another when the stent is in an unexpanded state. Optionally, all cylindrical segments which are adjacent one another along the length of the stent are in overlapping relationship when the stent is in an unexpanded state. The stent segments may be any suitable segments including serpentine segments and/or segments comprising a plurality of cells with openings therethrough. Desirably, the segments are arranged in a herringbone pattern. In another arrangement, the first segment is of a first radius and the second segment is of a second radius smaller than the first segment. Optionally, the stent may comprise a plurality of overlapping segments which alternate in radius.

The invention is also directed to stents comprising a plurality of segments which are disposed in a herringbone pattern.

In another embodiment, the invention is directed to a method of producing a stent comprising the steps of providing a corrugated member having a first end, a second end and a longitudinal axis and processing the member into a stent, the processing step including removing material from the corrugated member so as to form a desired stent pattern. Desirably, the corrugated member may be a tube or a sheet. Where the member is a sheet, the processing step further includes the step of forming a tube from the corrugated member. The material may be removed during the processing step by any suitable technique including cutting, laser etching, chemical etching and electrical discharge milling. Desirably, the corrugations extend longitudinally. Also desirably, the corrugations extend from the first end of the member to the second end of the tube, longitudinally, spirally or otherwise.

The invention is also directed to stents made in accordance with the inventive methods disclosed herein.

Additional details and/or embodiments of the invention are discussed below.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
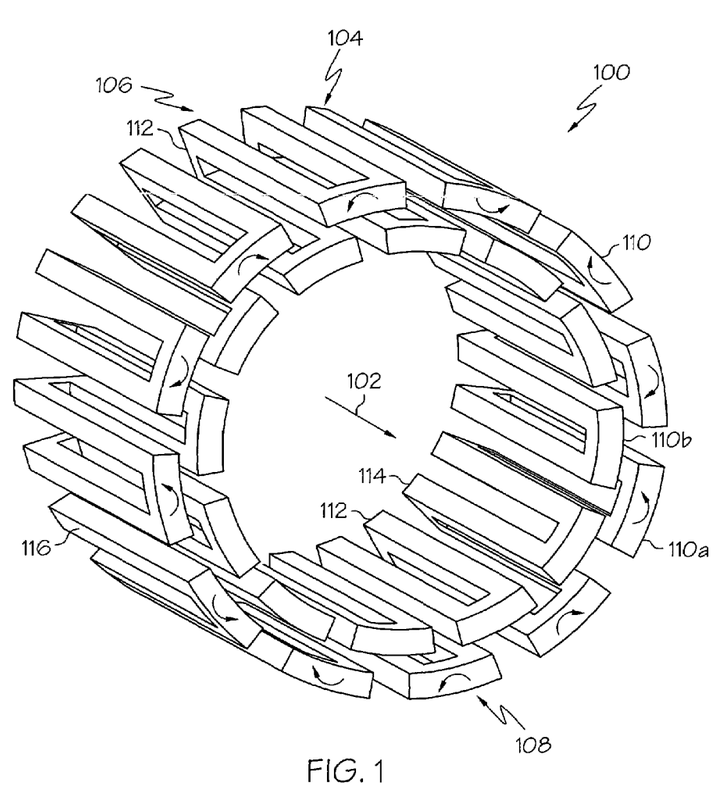
FIG. 1 is a perspective view of an inventive stent in an unexpanded configuration.

Turning to FIG. 1, a stent is shown generally at 100 in an unexpanded state. Stent 100, with longitudinal axis 102 therethrough, comprises at least one segment 104 and desirably, a plurality of segments 104. Segment 104, having a proximal end 106 and a distal end 108, may be any suitable stent segment. Segment 104 may be capable of supporting a lumen by itself or may only be capable of supporting a bodily lumen in conjunction with other segments. The segment may be rigid or flexible. As shown in FIG. 1, segment 104 is a serpentine segment comprising a plurality of peaks 110 and troughs 112. Peaks 110 are disposed at distal end 108 of segment 104. Troughs 112 are disposed at proximal end 106 of segment 104. Peaks 110 including first peaks 110a and second peaks 110b arranged in an alternating pattern about the longitudinal axis 102 of the stent. First peaks 110a are disposed at a first distance from the longitudinal axis of the stent and second peaks 110b are disposed at a second distance from the longitudinal axis of the stent. The second distance is less than the first distance. As shown in FIG. 1, first peaks 110a define a substantially cylindrical outer surface of segment 104.

Figure 2:
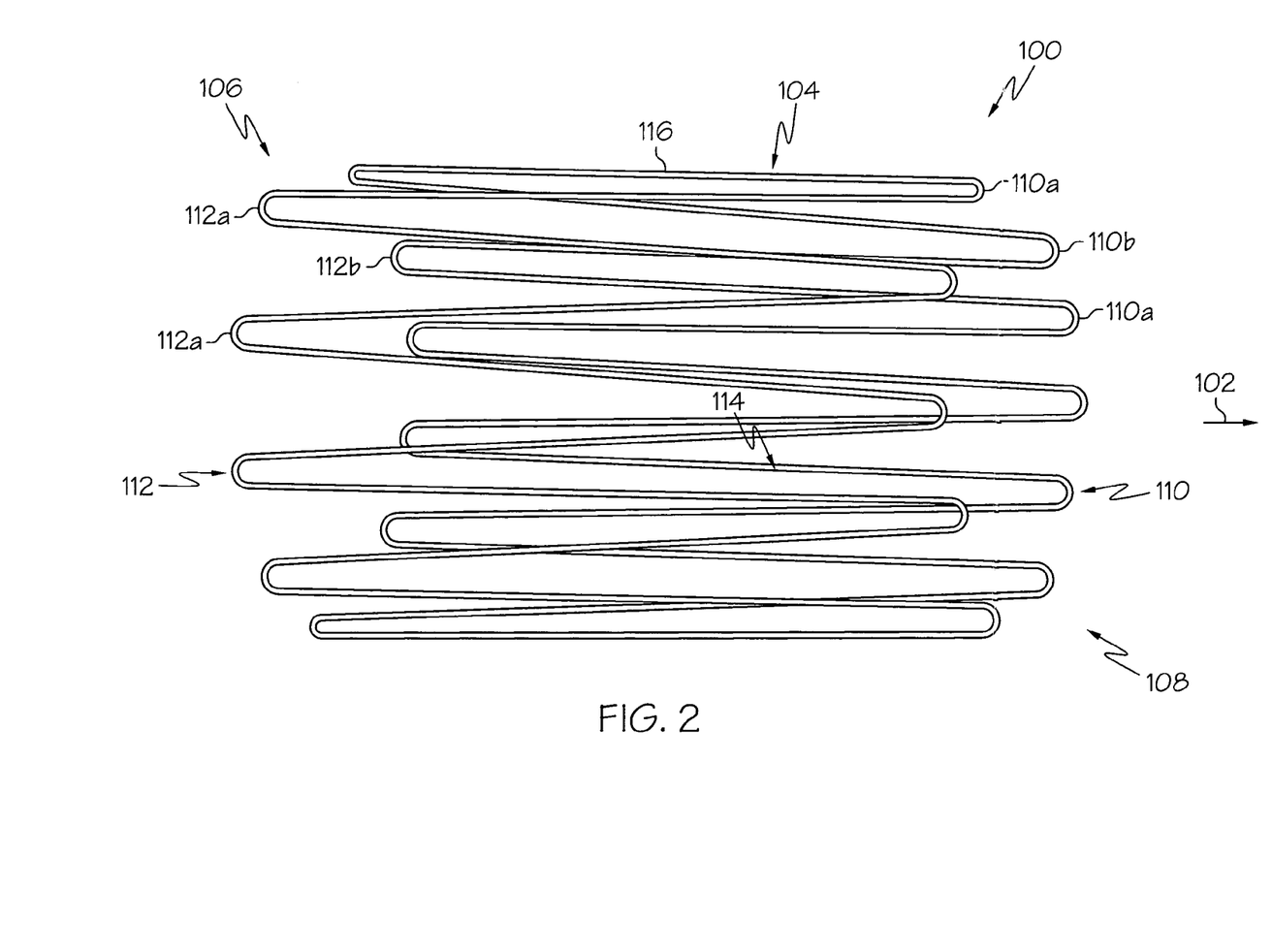
FIG. 2 is a perspective view of an embodiment of the invention in an expanded configuration.

Stent 100 is expandable from a first unexpanded configuration, as shown in FIG. 1 to a second expanded configuration of enlarged cross-section as shown in FIG. 2. In the expanded configuration, desirably, the first and second peaks are equidistant from the longitudinal axis of the stent.

In the embodiment of FIG. 1, as well as other embodiments, second peaks 110b and optionally, second troughs 112 define a substantially cylindrical inner surface of the segment. The substantially cylindrical inner surface 114 of the segment may be of constant diameter as shown in FIG. 1 or may taper outward toward the substantially cylindrical outer surface 116 of the segment.

The stent of FIG. 1 may comprise a single segment or a plurality of segments where adjacent segments are interconnected one to the other via one or more connectors. The connectors may be straight or curved, having one or more bends therein. The connectors may lie entirely on the tubular outer surface of the stent as defined by the segments or may deviate therefrom and include substantial radial components.

Figure 3:
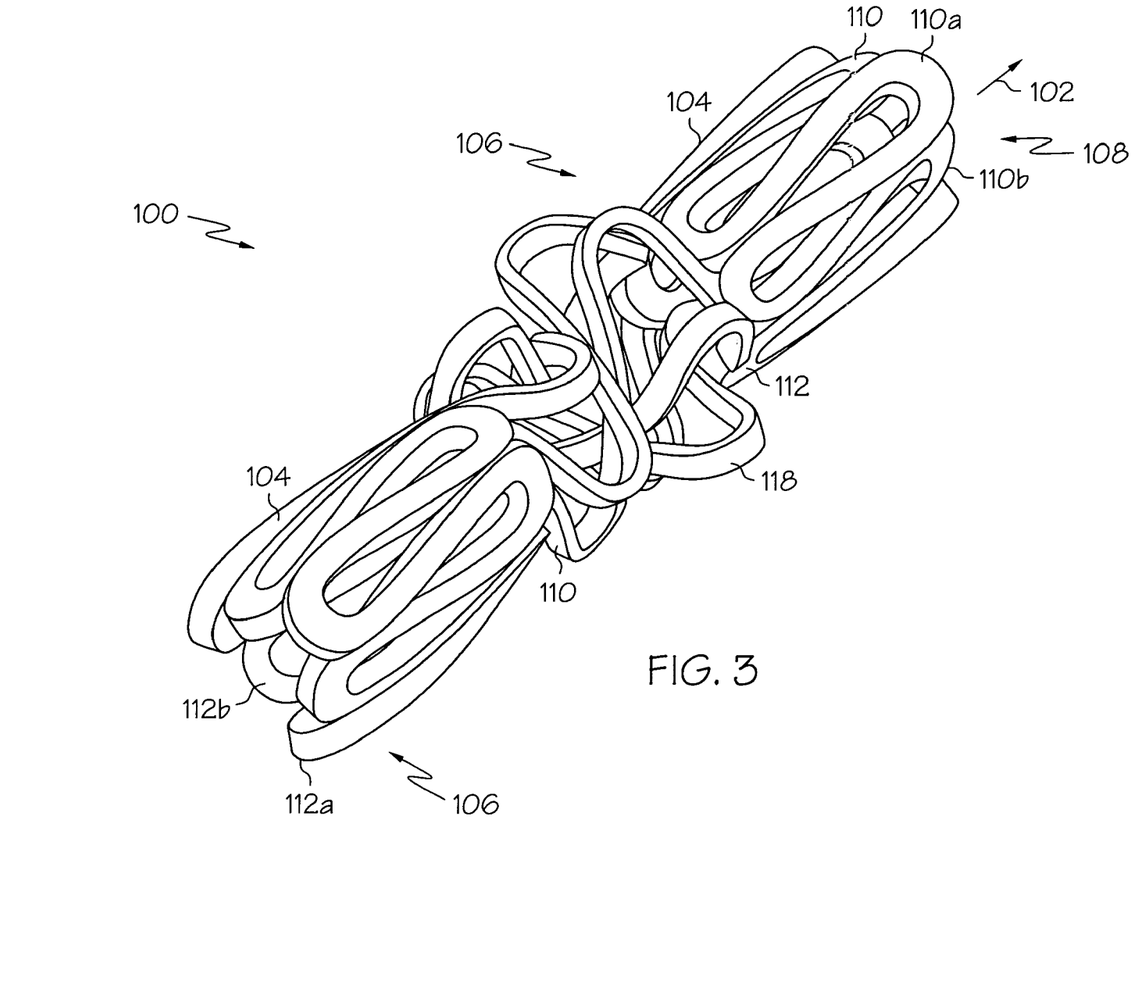
FIG. 3 is a perspective view of an inventive stent in an unexpanded configuration.
Figure 4:
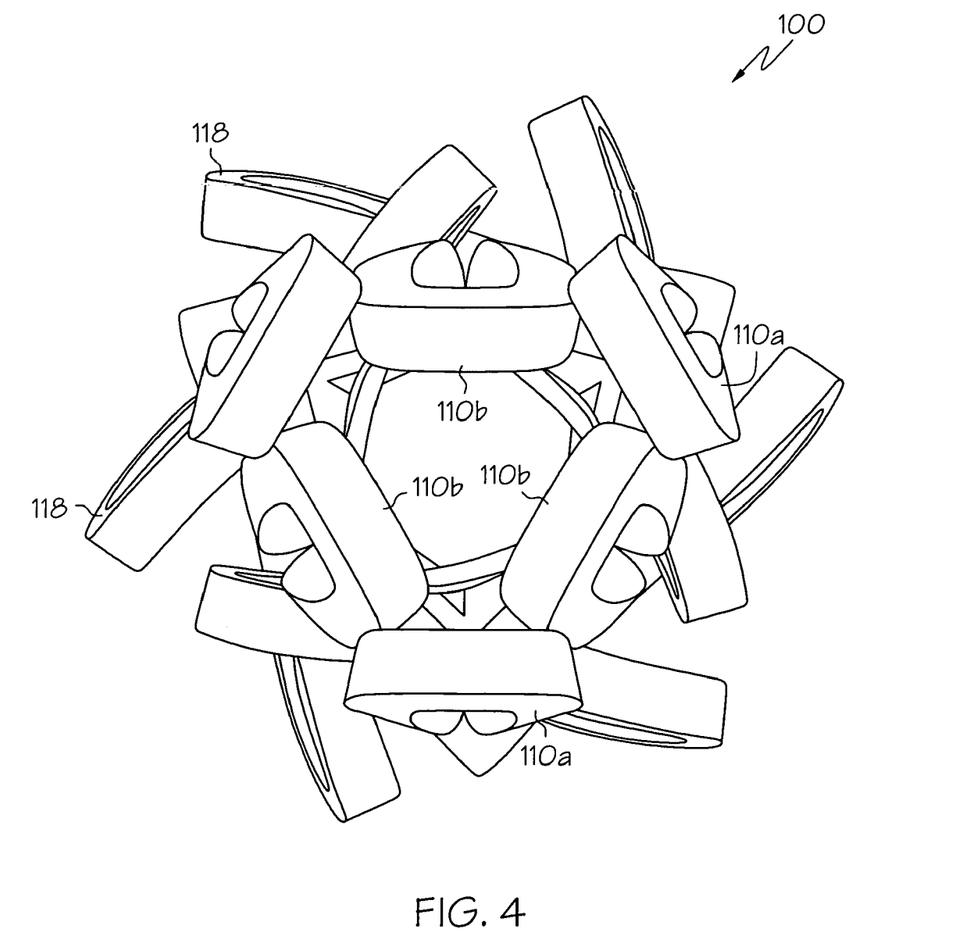
FIG. 4 is an end view of the stent of FIG. 3.

The inventive stents and inventive stent segments may assume other configurations as well. Another such stent and segment configuration is shown in FIGS. 3 and 4. Stent 100, having a proximal end 106 and a distal end 108, is formed of two segments 104 which are connected via connectors 118. Each segment 104 comprises a plurality of alternating peaks 110 located at the distal end of each segment and troughs 112 located at the proximal end of each segment. Distal most segment 104 comprises first peaks 110a and second peaks 110b. First peaks 110a are disposed at a first distance from the longitudinal axis of the stent and second peaks 110b are disposed at a second distance from the longitudinal axis of the stent. The second distance is different from the first distance. As shown in FIGS. 3 and 4, first peaks 110a define a substantially cylindrical outer surface of segment 104. Second peaks 110b form every second peak.

Proximal most segment 104 comprises first troughs 112a and second troughs 112b. First troughs 112a are disposed at a first distance from the longitudinal axis of the stent and second troughs 112b are disposed at a second distance from the longitudinal axis of the stent. The second distance is less than the first distance. As shown in FIG. 3, first troughs 112a define a substantially cylindrical outer surface of segment 104. Second troughs 112b form every second trough. More generally, the second trough may form every nth trough where n is an integer greater than 1.

Preferably, the various embodiments of the invention may include any pattern of alternating troughs and/or peaks as may be desired. It should noted that the term "alternating" may be used to describe any regular or irregular pattern of peaks and/or troughs as may be desired.

As shown in FIGS. 3 and 4, segments 104 are connected by one or more connectors 118. Connector 118 is curved and extends out of the outer surface of the stent defined by segments 104. Other types of connectors may also be used. For example, the connector may be straight or may have one or more portions which are curved or have bends therein. An example of straight connectors is shown in WO 9626689. An example of a connector having bends is shown in U.S. Pat. No. 6,152,957. The ends of the connector may be circumferentially aligned one with the other or may be circumferentially displaced one from the other. An example of the latter is shown in WO 9626689. The connectors may lie entirely along the tubular surface of the stent defined by the stent segments or may deviate therefrom.

The invention also contemplates stents comprising a single such segment 104 as well as stents comprising two or more of segments 104.

Figure 5:
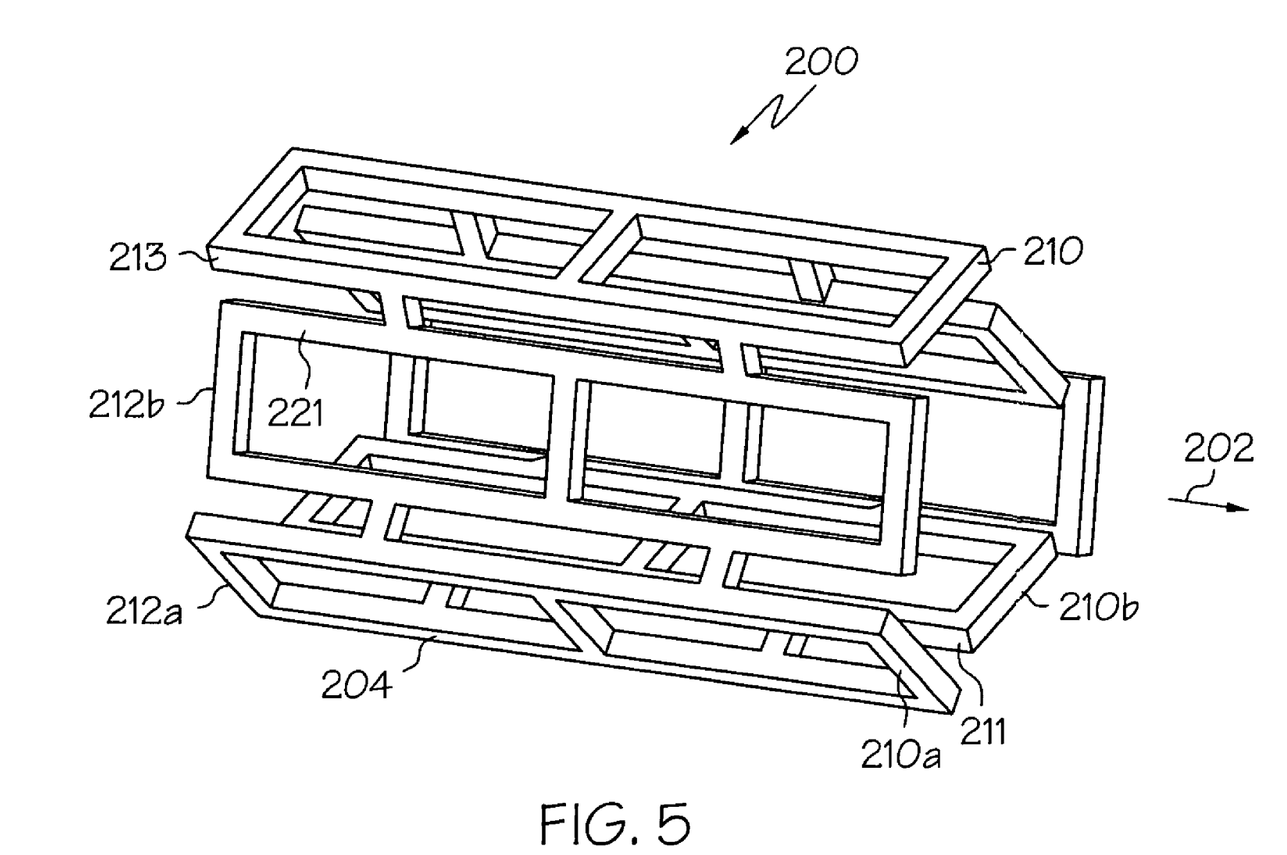
FIG. 5 is a perspective view of another embodiment of the invention in unexpanded form.

The invention is also directed to a stent, such as that shown generally at 200 in FIG. 5 in an unexpanded configuration, comprising at least one segment 204 having a plurality of distal closed portions 210 and distal open portions 211 alternating with one another. Distal closed portions 210 including first distal closed portions 210a disposed at a first distance from the longitudinal axis 202 of the stent and second distal closed portions 210b disposed at a second distance from the longitudinal axis of the stent. The second distance is less than the first distance. First distal closed portions 210a and second distal closed portions 210b alternate with one another about the longitudinal axis of the stent. First closed portions 210a define a substantially cylindrical outer surface of the segment. The proximal end of the segment comprises a plurality of proximal closed portions 212 and proximal open portions 213 alternating with one another.

The second distal closed portions may define a substantially cylindrical inner surface of the segment. Optionally, the substantially cylindrical inner surface of the segment may taper outward toward the substantially cylindrical outer surface of the segment.

Figure 6:
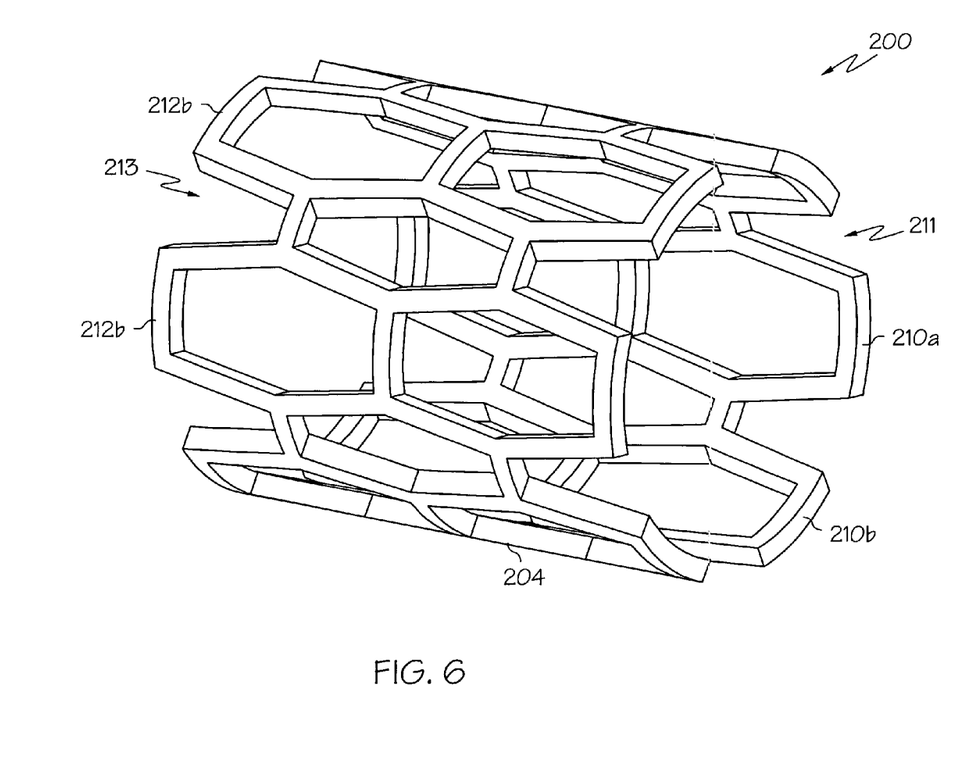
FIG. 6 is a perspective view of the stent of FIG. 5 in expanded form.

Desirably, in the expanded configuration, as shown in FIG. 6, first distal closed portions 210a and second distal portions 210b are equidistant from the longitudinal axis of the stent.

As further shown in FIG. 5, proximal closed portions 212 may include first proximal closed portions 212a disposed at a first distance from the longitudinal axis of the stent and second proximal closed portions 212b disposed at a second distance from the longitudinal axis of the stent. The second distance is less than the first distance. The first and second proximal closed portions alternate with one another about the longitudinal axis of the stent.

Any suitable segment may be used in the practice of the invention. As shown in FIG. 5, segment 204 may include a plurality of cells 221 with openings therethrough. The cells may be of any suitable geometry. Another example of a suitable segment is a serpentine segment, for example, segment 104 of FIG. 1 or segment 104 of FIG. 3. Proximal closed portions 212 may be aligned with distal closed portions 210 as shown in FIG. 5. The invention also contemplates segments in which proximal closed portions are not aligned with distal closed portions.

Figure 7:
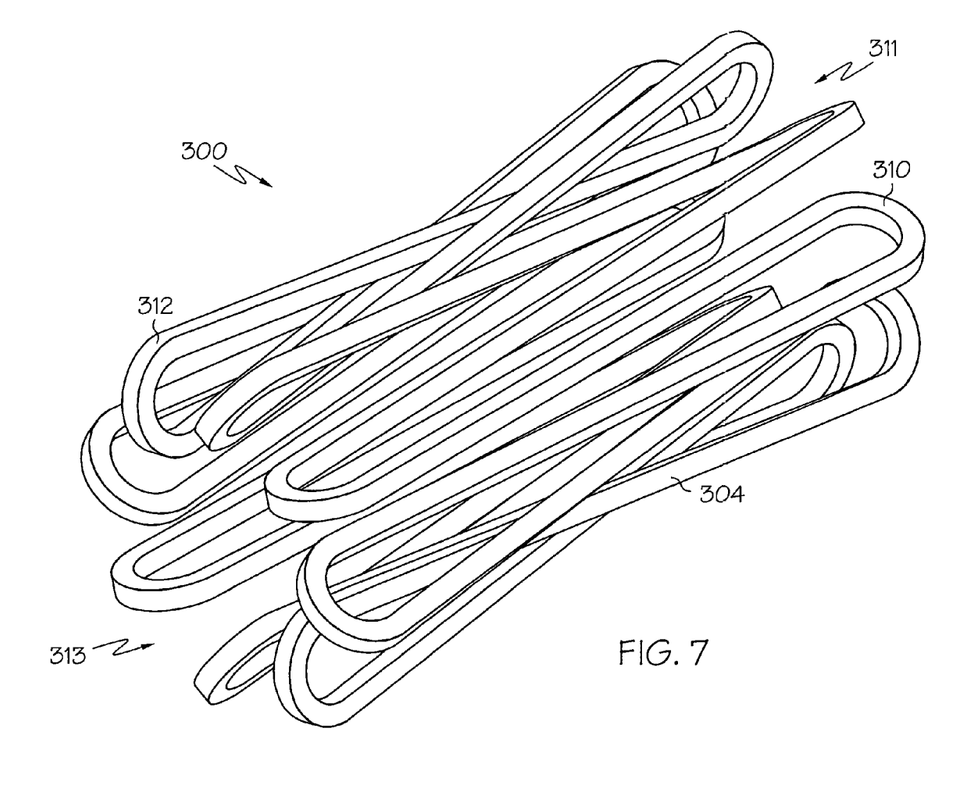
FIG. 7 is a perspective view of another embodiment of the invention in unexpanded form.
Figure 8:
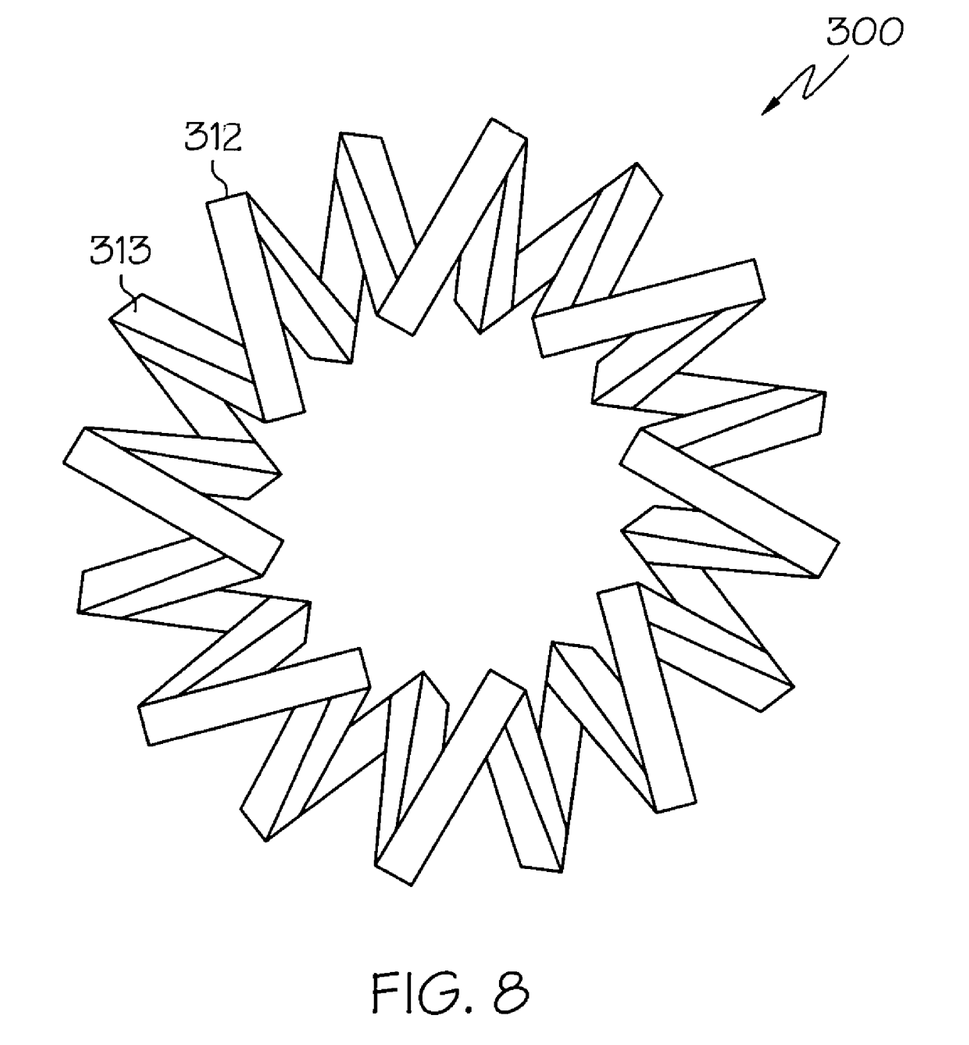
FIG. 8 is an end view of an inventive stent similar to that shown in FIG. 7.

In yet another embodiment, the invention is directed to a stent such as that shown at 300 in an unexpanded configuration in FIGS. 7 and 8 comprising at least one segment 304 having a proximal end and a distal end. The distal end of segment 304 comprises a plurality of distal closed portions 310 and distal open portions 311 alternating with one another. Distal closed portions 310 which are adjacent one another are arranged in overlapping relationship about the segment. The proximal end of the segment comprises a plurality of proximal closed portions 312 and proximal open 313 portions alternating with one another.

Each distal closed portion 310 extends at least partially radially inward. The segment may be serpentine, as shown in FIGS. 7 and 8 or may be of any other suitable construction including of cellular construction having a plurality of cells with openings therethrough as shown in FIG. 3, suitably modified.

The stent may comprise a single segment as shown in FIG. 7 or a plurality of segments. Where a plurality of segments are provided, segments 304 which are adjacent one another are connected one to the other via one or more connectors 314.

In yet another embodiment, the invention is directed to a stent comprising a plurality of segments which define a cylindrical surface of the stent and which are connected one to the other by one or more connectors which deviate from the tubular surface of the stent. An example of such a stent is shown in FIG. 3. Stent 100 comprises two segments 104 with a plurality of connectors 118 extending therebetween. Connectors 118 deviate from the cylindrical surface of the stent and include a portion which extends in a radial direction. Connectors 118 as shown in FIG. 3 are curved and include a plurality of bends. The invention also contemplates connectors which are straight and connectors which include only a single bend. The first and second ends of each connector may be longitudinally and circumferentially offset or may be longitudinally offset and circumferentially aligned. Any suitable segment may be used including any of those disclosed above. Desirably, the connectors lie on the tubular surface of the stent when the stent is in the expanded state.

Figure 9:
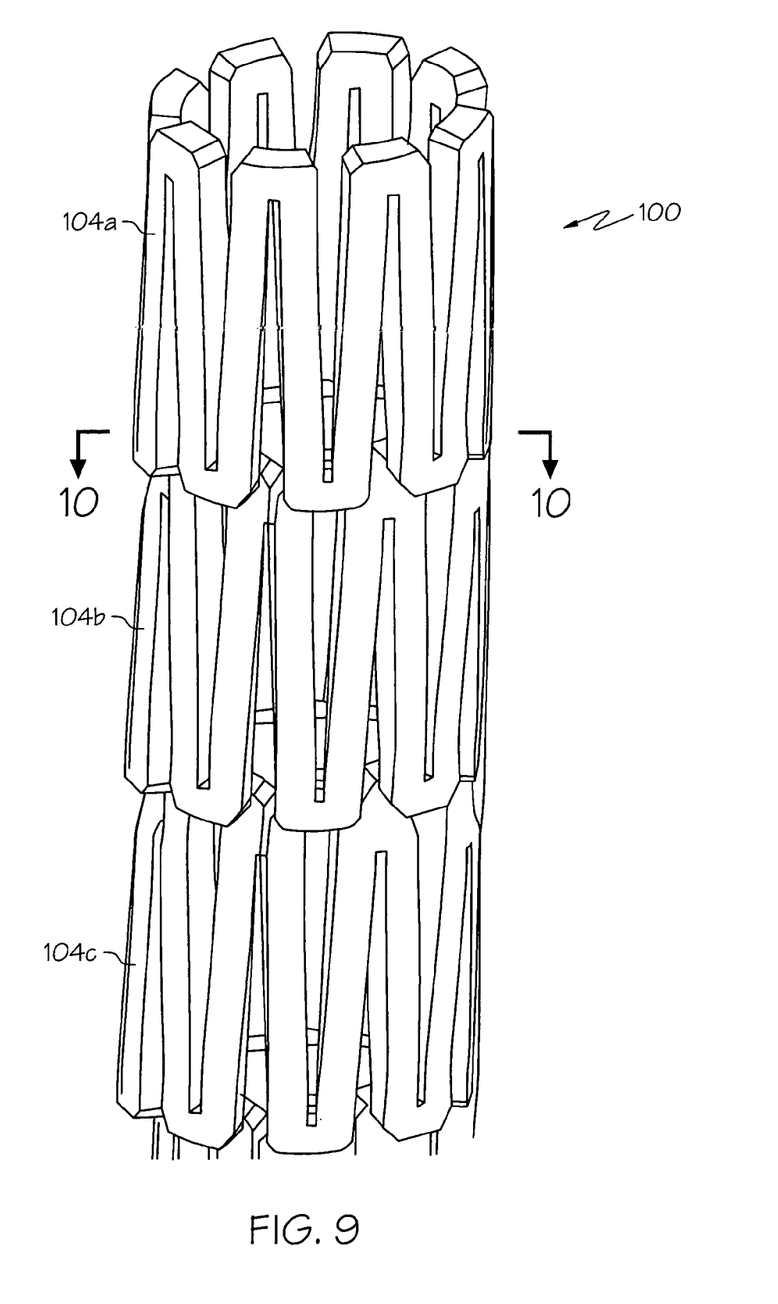
FIG. 9 is a perspective view of an inventive stent.
Figure 10:
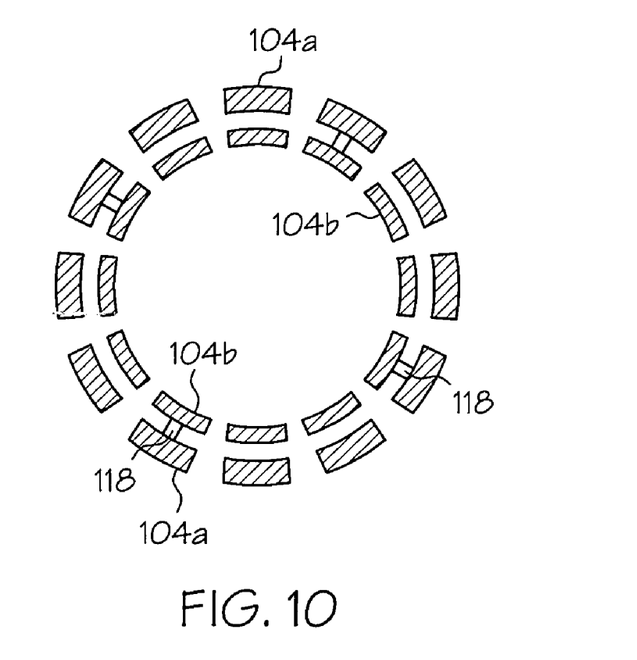
FIG. 10 is a cross-sectional view of the stent of FIG. 9 taken along line 10—10.
Figure 11:
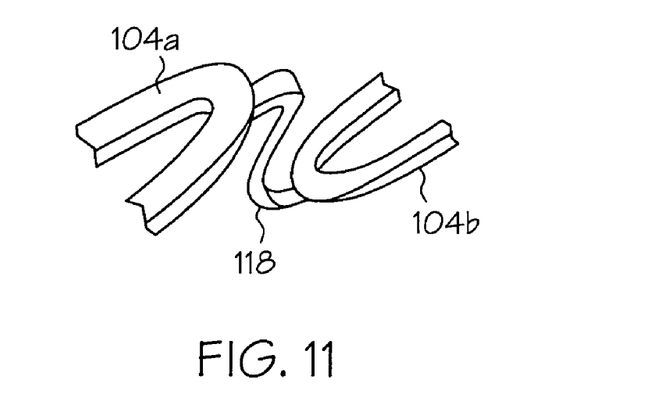
FIG. 11 is a schematic illustrating the connectors which extend between adjacent segments in the stent of FIG. 9.

The invention is also directed to a stent such as that shown generally at 100 in FIG. 9, comprising a plurality of cylindrical segments 104a–c each of which comprises a plurality of interconnected struts. The cylindrical segments include a first cylindrical segment 104a, a second cylindrical segment 104b connected to first cylindrical segment 104a and a third cylindrical segment 104c connected to second cylindrical segment 104b. As shown in FIG. 9, first cylindrical segment 104a and second cylindrical segment 104b at least partially overlap with one another and second cylindrical segment 104b and third cylindrical segment 104c at least partially overlap with one another when the stent is in an unexpanded state. The stent segments are disposed in a herringbone arrangement. Adjacent segments are connected one to the other via one or more connectors. Connectors 118, as shown in FIGS. 10 and 11 are curved and extend from every third peak region of one segment to every third trough region of an adjacent segment. More generally, the connectors may be in the form of any of the other connectors disclosed herein and may extend from regions other than the peaks and troughs. Moreover, any number of connectors may extend between adjacent segments ranging from one connector up to twice the number of peaks in the segment.

Desirably, upon expansion of the stent, the segments no longer overlap one another. This may be achieved by employing curved connectors which are flexible. Straight connectors which are flexible may also be used.

The extent of overlap between segments of the stent of FIG. 9 is exemplary. It is also within the scope of the invention to have more overlap between adjacent segments of the stent. For example, the length of the overlap region between adjacent segments may range from 0% to 75% or more of the length of each segment.

Stent 100 may include any suitable segments including serpentine segments such as those shown in FIG. 3 or segments comprising a plurality of cells with openings therethrough such as that shown in FIG. 6. The cylindrical segments may optionally include overlapping struts.

The invention is also directed to stents which comprise a plurality of segments which are disposed in a herringbone pattern. An example of such a stent is shown in FIG. 9.

Figure 12:
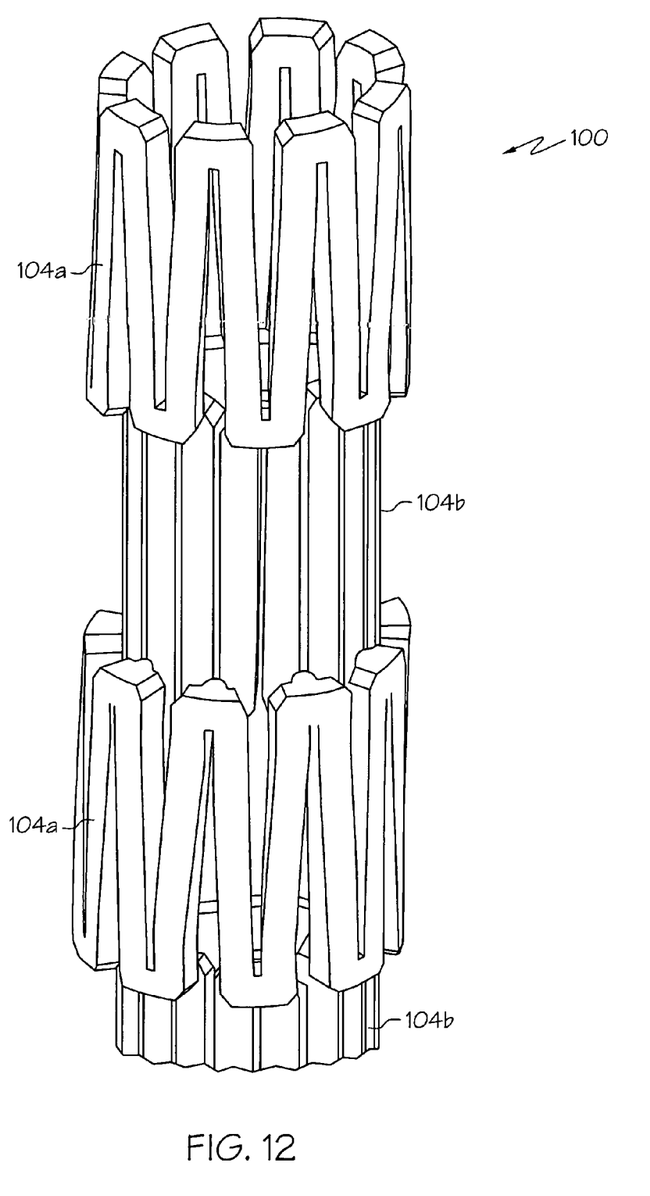
FIG. 12 is a perspective view of another inventive stent.
Figure 13:
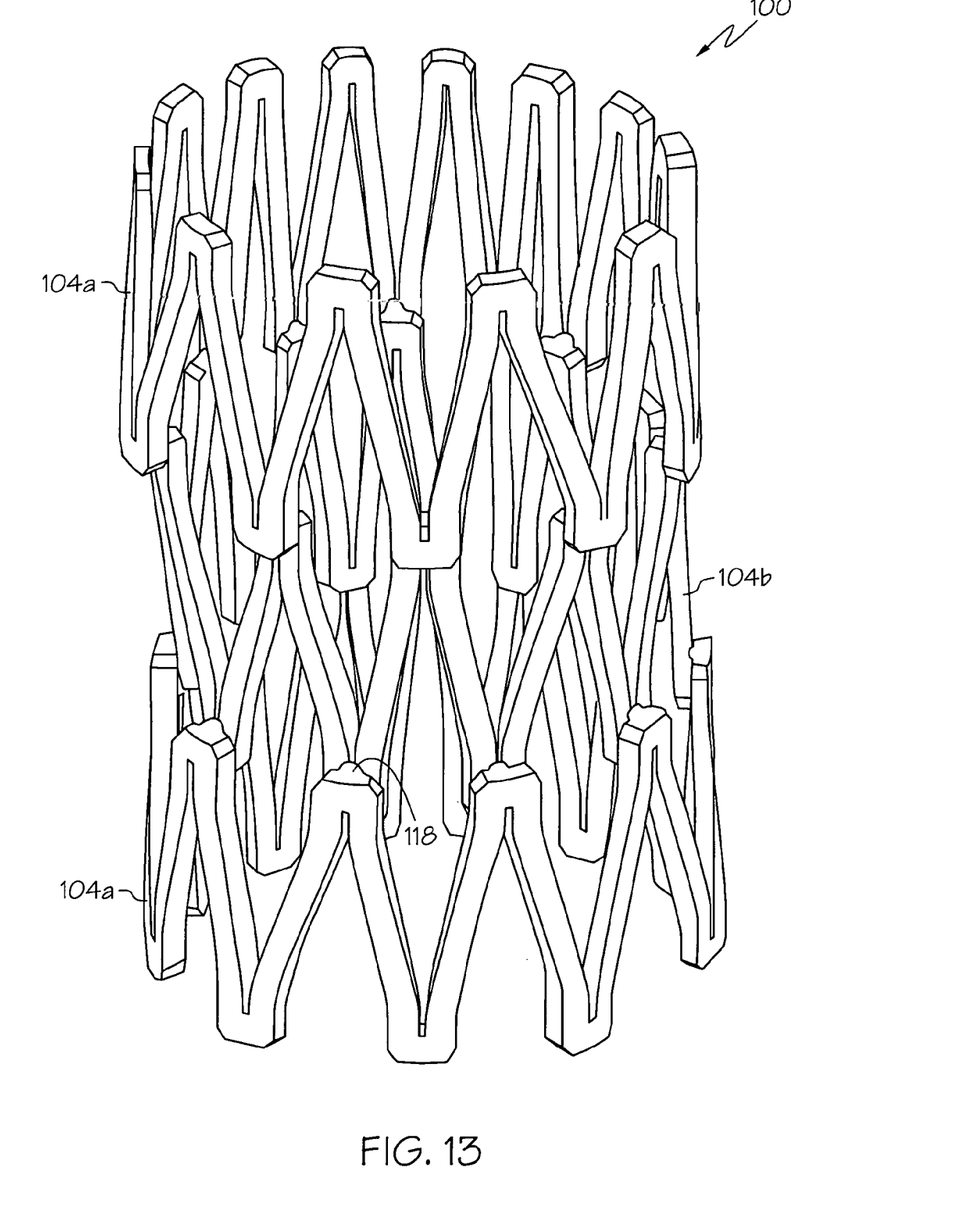
FIG. 13 is a perspective view of a partially expanded stent similar to that shown in FIG. 12 in the unexpanded state.

Another example of a stent with overlapping segments in the unexpanded state is shown at 100 in FIG. 12 and in a partially expanded state in FIG. 13. Stent 100 comprises two segments 104a of a first radius and one segment 104b of a second radius smaller than the first segment. The stent may further comprise additional first segments and seconds disposed in an alternating relationship. Adjacent segments are connected to one another via one or more connectors 118 which extend from peak regions to trough regions. As shown in FIGS. 12 and 13, each peak is connected to a trough region via a connector. Any of the connectors disclosed herein may be used to connect adjacent segments together. Desirably, curved connectors such as those shown in FIG. 11 will be used.

As with the embodiment of FIG. 9, the overlap between adjacent segments of the stent of FIGS. 12 and 13, disappears upon further expansion of the stent.

The extent of overlap between segments of the stent of FIG. 12 is exemplary. It is also within the scope of the invention to have more overlap between adjacent segments of the stent. For example, the length of the overlap region between adjacent segments may range from 0% to 75% or more of the length of each segment.

Stent 100 may include any suitable segments including serpentine segments such as those shown in FIG. 3 or segments comprising a plurality of cells with openings therethrough such as that shown in FIG. 6. The cylindrical segments may optionally include overlapping struts.

The inventive stents with overlapping segments may be designed such that the increase in the length of the stent upon expansion of the stent resulting from the segments ceasing to overlap offsets any foreshortening of the individual segments so that the stent remains constant in length in the expanded state.

The invention is directed to any of the above stents whether in the unexpanded state or in the expanded state.

The inventive stents, in many of the embodiments disclosed herein, are characterized by a reduced delivery profile as compared with stents which do not have overlapping segments. This reduced profile facilitates delivery of the stent.

The inventive stents, in many of the embodiments disclosed herein, are also characterized by an increased flexibility when in the reduced profile. Typical prior art stents have a high concentration of metal or other stent material when crimped. This leaves little room for movement of the stent material which is necessary to accommodate flexing of the stent. The inventive multilayer stents, on the other hand, are characterized by a lower concentration of metal or other stent material which provides additional room for movement of the stent material and hence, enhanced flexibility.

The inventive stents disclosed herein may be made of any stent material known in the art including polymeric materials, metals, ceramics and composites. Suitable polymeric materials include thermotropic liquid crystal polymers (LCP's). Where the stent is made of metal, the metal may be stainless steel, cobalt chrome alloys such as spring steel, elgiloy, tantalum or other plastically deformable metals. Other suitable metals include shape-memory metals such as nickel-titanium alloys generically known as "nitinol", platinum/tungsten alloys and titanium alloys, as well as MRI compatible materials.

The inventive stents may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

The inventive stents may be coated in part or in its entirety with other biocompatible coatings such as lubricious coatings. The inventive stents may also be provided with drug-containing coatings which release drugs over time. Suitable coatings include a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Subjecting the stent to such a treatment also may prevent flaring of the ends of the stent during delivery of the stent. Mechanical retention devices may also be used to maintain the stent on the balloon during delivery.

Any suitable manufacturing process may be used for producing the inventive stents including laser cutting, chemical etching, electroforming or stamping of a tube. The inventive stents may also be manufactured by laser cutting, chemically etching, stamping or electroforming a flat sheet, rolling the sheet and welding the sheet, by electrode discharge machining, or by molding the stent with the desired design. The inventive stents may also be made by growing or extruding or winding a stent with the inventive patterns. Already existing stents may also be bent and/crimped into the inventive stent configurations.

In yet another embodiment, the invention is directed to a method of producing a stent comprising the steps of providing a corrugated member having a first end, a second end and a longitudinal axis and processing the member into a stent, the processing step including removing material from the corrugated member so as to form a desired stent pattern. Desirably, the corrugated member may be a tube or a sheet. Where the member is a sheet, the processing step further includes the step of forming a tube from the corrugated member. The material may be removed during the processing step by any suitable technique including cutting, laser etching, chemical etching, stamping and electrode discharge machining. Desirably, the corrugations extend longitudinally. Also desirably, the corrugations extend from the first end of the member to the second end of the tube, longitudinally, spirally or otherwise. The stent pattern may include serpentine segments and/or cellular segments such as, but not limited to, those disclosed above.

The invention is also directed to stents made in accordance with the inventive methods disclosed herein.

The inventive stents may be provided in mechanically expandable form, in self-expanding form or as a hybrid of the two. Mechanically expandable stents, in accordance with the invention, may be expanded using any suitable mechanical device including a balloon.

The inventive stents may be used for coronary arteries, peripheral arteries, arteries of the neck and intracranial arteries. More generally, the inventive stents may be used for any vessel of the human body including but not limited to arteries, veins, biliary ducts, urethras, fallopian tubes, bronchial tubes, the trachea and the esophagus.

Suitable stent delivery devices such as those disclosed in U.S. Pat. No. 6,123,712, U.S. Pat. No. 6,120,522 and U.S. Pat. No. 5,957,930 may be used to deliver the inventive stents to the desired bodily location. The choice of delivery device will depend on whether a self-expanding or balloon expandable stent is used.

The inventive stents may also be used as the framework for a graft. Suitable coverings include nylon, collagen, PTFE and expanded PTFE, polyethylene terephthalate and KEVLAR, or any of the materials disclosed in U.S. Pat. No. 5,824,046 and U.S. Pat. No. 5,755,770. More generally, any known graft material may be used including synthetic polymers such as polyethylene, polypropylene, polyurethane, polyglycolic acid, polyesters, polyamides, their mixtures, blends, copolymers, mixtures, blends and copolymers.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

The particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent having a reduced state and an expanded state, and further having longitudinal axis therethrough, the stent comprising at least one serpentine segment having a proximal end and a distal end, the serpentine segment comprising a plurality of peaks and troughs, in the reduced state a plurality of first peaks disposed at a first distance from the longitudinal axis of the stent and a plurality of second peaks disposed at a second distance from the longitudinal axis of the stent, the second distance less than the first distance, in the expanded state the first distance being substantially the same as the second distance, the first peaks defining a substantially cylindrical outer surface of the segment.

2. The stent of claim 1 wherein the troughs include first troughs and second troughs arranged in a regular alternating pattern about the longitudinal axis, the first troughs disposed at a first distance from the longitudinal axis of the stent, the second troughs disposed at a second distance from the longitudinal axis of the stent, the second distance different from the first distance.

3. The stent of claim 1 comprising a plurality of serpentine segments.

4. The stent of claim 3 wherein serpentine segments which are adjacent one another are connected one to the other.

5. The stent of claim 1 wherein the second peaks define a substantially cylindrical inner surface of the segment.

6. The stent of claim 5 wherein the substantially cylindrical inner surface of the segment tapers outward toward the substantially cylindrical outer surface of the segment.

* * * * *